United States Patent [19]

Isshiki et al.

[11] Patent Number: 4,544,511
[45] Date of Patent: Oct. 1, 1985

[54] PROCESS FOR PRODUCING ACETIC ANHYDRIDE

[75] Inventors: Tomiya Isshiki, Tokyo; Yasuhiko Kijima; Yuh Miyauchi, both of Chiba; Takao Kondo, Tokyo, all of Japan

[73] Assignee: Mitsubishi Gas Chemical Company, Inc., Tokyo, Japan

[21] Appl. No.: 704,909

[22] Filed: Feb. 22, 1985

Related U.S. Application Data

[63] Continuation of Ser. No. 518,770, Aug. 2, 1983, abandoned, which is a continuation of Ser. No. 334,241, Dec. 24, 1981, abandoned.

[30] Foreign Application Priority Data

Dec. 26, 1980 [JP] Japan ................................ 55-188729
Feb. 4, 1981 [JP] Japan .................................. 56-49692

[51] Int. Cl.⁴ ............................................. C07C 51/12
[52] U.S. Cl. .................................................. 260/549
[58] Field of Search ........................................ 260/549

[56] References Cited

U.S. PATENT DOCUMENTS

| 2,729,651 | 1/1956 | Reppe et al. | 260/343.5 |
| 4,002,677 | 1/1977 | Rizkalla | 260/549 |
| 4,002,678 | 1/1977 | Rizkalla | 260/549 |

OTHER PUBLICATIONS

Stull, Daniel R. et al., *The Chemical Thermodynamics of Organic Compounds,* (1969), John Wiley & Sons, Publ., pp. 218–219, 422–423 and 448–451.

*Primary Examiner*—Natalie Trousof
*Assistant Examiner*—L. Hendriksen
*Attorney, Agent, or Firm*—Fleit, Jacobson, Cohn & Price

[57] ABSTRACT

A process for producing acetic anhydride which comprises reacting methyl acetate or dimethyl ether with carbon monoxide in the presence of a catalyst comprising (a) nickel or a nickel compound, (b) at least one halide selected from the group consisting of bromides, iodides and mixtures thereof and (c) at least one organic nitrogen group compound and together with a specific co-catalyst is disclosed. According to this invention acetic anhydride is produced by using highly active non-expensive catalyst and co-catalyst.

18 Claims, No Drawings

PROCESS FOR PRODUCING ACETIC ANHYDRIDE

This application is a continuation of application Ser. No. 518,770, filed Aug. 2, 1983 now abandoned, which is a continuation of application Ser. No. 334,241, filed 12/24/81, now abandoned.

BACKGROUND OF THE INVENTION

This invention relates to a process for producing acetic anhydride which comprises reacting methyl acetate or dimethyl ether with carbon monoxide in the presence of a catalyst and a co-catalyst.

In the prior art, the known catalysts for producing carboxylic anhydrides from carboxylic esters or ethers and carbon monoxide include the following:
(i) a catalyst comprising a noble metal belonging to Group VIII of the Periodic Table, such as rhodium, a halide and a third component as disclosed in Japanese Patent Publication (Kokoku) No. 3926/1977; Japanese Patent Publication (Kokai) No. 65709/1976 and Japanese Patent Publication (Kokai) No. 115403/1976, and
(ii) a catalyst comprising nickel or cobalt, a halide and a third component as disclosed in Japanese Patent Publication (Kokai) No. 59214/1979 assigned to the assignee of this application, U.S. Pat. Nos. 4,002,677, 4,002,678 and 2,729,651.

However, catalyst (i) contains expensive rhodium as shown in Hydrocarbon Processing 54, June 83 (1975).

In case of producing carboxylic anhydrides from carboxylic esters or ethers and carbon monoxide by using a rhodium catalyst, a rhodium complex has to be prevented from being reduced to metallic rhodium under a reducing atmosphere as disclosed in KAKTAF, 29 (5), page 376 (1976) or the rhodium component has to be prevented from being scattered from the reaction system during the operation of separating the product as disclosed in Japanese Patent Publication (Kokai) No. 90204/1978.

In Japanese Patent Publication (Kokai) No. 59214/1979 assigned to the assignee of this invention, a nickel catalyst has been proposed in place of the noble metal catalyst. However, when using catalyst (ii) as disclosed in Japanese Patent Publication (Kokai) No. 59214/1979 and U.S. Pat. No. 2,729,651 the reaction rate is low, and the reaction conditions are severe.

SUMMARY OF THE INVENTION

The present inventors carried out research to increase the rate of reaction between methyl acetate or dimethyl ether and carbon monoxide and to use the reaction catalyst (ii) under milder reaction conditions. As a result we found a process for producing acetic anhydride from methyl acetate or dimethyl ether and carbon monoxide in the presence of a catalyst comprising nickel or a nickel compound, a halide and an organic nitrogen group compound and a co-catalyst comprising one or more materials selected from the group consisting of the metals belonging to Groups IA, IIIB and IVB of the Periodic Table, compounds of the metals and mixtures thereof and optionally a metal belonging to Group IIA of the Periodic Table and compounds of the metals.

This invention relates to a process for producing acetic anhydride which comprises reacting methyl acetate or dimethyl ether with carbon monoxide in the presence of a catalyst and a co-catalyst, said catalyst comprising (a) nickel or a nickel compound, (b) a halide or halides selected from bromides, iodides or mixtures thereof and (c) an organic nitrogen group compound; and said co-catalyst comprising one or more metals belonging to Groups IA, IIIB and IVB of the Periodic Table, compounds of the metals and mixtures thereof and optionally one or more metals belonging to IIA of the Periodic Table, compounds of the metals and mixtures thereof.

DETAILED DESCRIPTION OF THE INVENTION

By the "Periodic Table" given in the specification and the claims is meant Periodic Table in "Shin Jikken Kagaku Kohza" vol. 12, 1976 pages 4–5 published by the Japan Chemical Association.

Nickel or nickel compounds (sometimes hereinunder referred to as nickel component) constituting the catalyst of this invention include organic or inorganic nickel compounds or metallic nickel. Examples of nickel and nickel compounds include nickel powder, nickel acetate, nickel iodide, nickel acetylacetonate, nickel tetracarbonyl, nickel dicarbonyl, nickel dicarbonyl bistriphenyl phosphine and tetramethyl ammonium nickel iodide.

Halides employed together with the nickel component include bromides, iodides or mixture thereof. Examples of the halides include alkyl halide, such as methyl iodide, acid halogenides, such as acetyl iodide, or hydrogen halides, such as hydrogen iodide, or mixtures thereof. The halide may be added to a reaction medium as it is. Materials which can be converted to an alkyl halide, an acid halogenide or hydrogen halide can be used as a halide constituting the catalyst of this invention. Examples of the materials which can be converted to an alkyl halide, an acid halogenide or a hydrogen halide by reacting with components in the reaction medium include inorganic halides, such as alkali metal halides, such as lithium, sodium or potassium halides; alkaline earth metal halides, such as magnesium or calcium halides; metal halides such as aluminum, zinc, copper, lanthanum, or cerium halides; or bromine or iodine. When halides of metals belonging to Groups IA, IIA, IIIB or IVB of the Periodic Table are used as a halide constituting the catalyst of this invention, they also serve as a component constituting the co-catalyst of this invention. Of the halides, methyl halides, such as methyl iodide, are preferable, because the use of these compounds makes easy the selection of corrosion-resistant reactor and separation of the reaction product from the reaction mixtures and purification of the reaction product.

Organic nitrogen group compounds are used together with the nickel component and the halide. The organic nitrogen group compounds include nitrogen, phosphorus, antimony or arsenic.

Examples of the organic nitrogen group compounds are shown in the following. However, compounds which are not listed in the following may be used as a promoter.

(I) Compounds of trivalent nigrogen group elements
(A) Compounds represented by the formula

wherein M is N, P, Sb or As.

(a) compounds wherein $R^1$, $R^2$ and $R^3$ may be the same or different, and are independently hydrogen, saturated alkyl having 1–10 carbon atoms, saturated cycloalkyl having 3–10 carbon atoms, or aryl having 6–10 carbon atoms.

M is N

The compounds include, for example, and amines, such as monomethyl amine, dimethyl amine, trimethyl amine, monoethylamine, diethyl amine, triethyl amine, dimethyl ethyl amine, tri-n-propyl amine, tri-iso-propyl amine, tri-n-butyl amine, tri-tert.-butyl amine, aniline, dimethyl aniline, diethyl aniline, dimethyl-benzyl amine, toluidine, triphenyl amine, cyclohexyl amine and the like.

M is P

The compounds include, for example, phosphines, such as tri-n-propyl phosphine, tri-iso-propyl phosphine, tri-n-butyl phosphine, tri-tert.-butyl phosphine, tricyclohexyl phosphine, triphenyl phosphine and the like.

M is Sb

The compounds include, for example, stibines, such as tri-iso-propyl stibine, ethyl-di-iso-propyl stibine, triphenyl stibine, tri(o-tolyl)stibine, phenyl diamyl stibine and the like.

M is As

The compounds include, for example, arsines, such as trimethyl arsine, triethyl arsine, tri-iso-propyl arsine, tri-n-propyl arsine, tricyclohexyl arsine, phenyl di-iso-propyl arsine, diphenyl arsine and the like.

(b) Wherein $R^1$ is hydrogen, alkyl having 1–10 carbon atoms, cycloalkyl having 3–10 carbon atoms, or aryl and $R^2$ and $R^3$ are taken together and represents methylene or polymethylene having 2–5 carbon atoms; the compounds include, for example, pyrrolidine, N-methyl pyrrolidine, piperidine or N-phenyl piperidine:

(c) wherein $R^1$ and $R^2$ may be the same or the different and independently represent hydrogen, alkyl having 1–10 carbon atoms, cycloalkyl having 3–10 carbon atoms, or aryl and having 6–10 carbon atoms and $R^3$ is aliphatic saturated acyl, or $R^1$ is hydrogen, alkyl having 1–10 carbon atoms, cycloalkyl having 3–10 carbon atoms or aryl having 6–10 carbon atoms, and $R^2$ and $R^3$ are taken together and represent lactam ring (in which $R^2$ and $R^3$ are bonded through carboxy polymethylene; the compounds include, for example carboxylamides such as acetamide, N, N-dimethylacetamide, acetanilide, N-methyl-N-phenylacetamide, and lactams, such as N-methyl-pyrrolidinone:

(d) wherein at least one of $R^1$, $R^2$ and $R^3$ is carboxymethyl and the remainder is hydrogen, alkyl having 1–10 carbon atoms, cycloalkyl having 3–10 carbon atoms or aryl having 6–10 carbon atoms; the compounds include, for example carboxylic acid derivatives, such as N, N-dimethyl glycine, N,N-diethyl glycine, iminodiacetic acid, N-methyl iminodiacetic acid, or nitrilo-triacetic acid:

(B) Organic compounds represented by the formula N≡CR wherein R represents an alkyl having 1 to 10 carbon atoms, a cycloalkyl having 3–10 carbon atoms or aryl; the compounds include for example nitriles, such as acetonitrile, propio-nitrile, or benzonitrile.

(C) Organic nitrogen group compounds represented by the formula

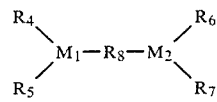

wherein $M_1$ and $M_2$ may the same or different and are independently N, P, Sb or As.

(a) wherein $R^4$, $R^5$, $R^6$ and $R^7$ may be the same or different and independently hydrogen, alkyl having 1–10 carbon atoms, cycloalkyl having 3–10 carbon atoms, or aryl and $R^8$ is methylene group or polymethylene group having 2–10 carbon atoms, phenylene, or carbonyl group $M^1$ and $M^2$ are N, P, Sb or As. The compounds include, for example, ethylene bis (disphenolphosphine), phenylene bis (dimethylphosphine), bis (diphenylarsino) ethane, bis (di-iso-propylarsino) hexane, bis (diethylstibino) pentane, N,N,N',N'-tetramethylethylenediamine, N,N,N',N'-tetraethylethylenediamine, N,N,N',N'-tetra-n-propylethylenediamine, N,N,N', N'-tetramethylmethylenediamine, N,N,N',N'-tetramethyl urea, N-methyl-2-pyrrodinone and triethylenediamine, (b) $R^4$ and $R^6$ may be the same or different and independently represent hydrogen, alkyl having 1–10 carbon atoms, cycloalkyl having 3–10 carbon atoms or aryl and $R^5$ and $R^7$ are taken together and represent methylene or polymethylene having 2–5 carbon atoms and $R^8$ is methylene or polymethylene having 2–5 carbon atoms; the compounds include, for example, heterocyclic compounds, such as piperazine, N-methyl-piperazine, N-ethylpiperazine, or 2-methyl-N, N'-dimethylpiperazine.

(c) other compounds include, for example, tris (diethylaminomethyl) stibine, 2,5-dicarboxy-piperazine, cyclohexane-1, 2-diamine-N,N,N',N'-tetraacetic acid or salts thereof, tetramethylester thereof, ethylene-diaminetetraacetic acid, or its salt or tetramethyl-ester thereof, 1,4-azabicyclo [2,2,2] octane, methyl substituted 1,4-diazabicyclo [2,2,2] octane, adiponitrile or N-methyl-morpholine.

(II) Hetero cyclic compounds include, for example, pyridines, such as pyridine; α-picoline, β-picoline, γ-picoline, 2-ethylpyridine, 3-ethylpyridine, 4-ethylpyridine, 2-propylpyridine, 4-propylpyridine, 4-butylpyridine, 4-isobutylpyridine, 4-tert.-butylpyridine, 2,6-lutidine, 2,4-lutidine, 2,5-lutidine, 3,4-lutidine, 3,5-lutidine, 2,4,6-collidine, 2-methyl-4-ethylpyridine, 2-methyl-5-ethylpyridine, 3-methyl-4-ethylpyridine, 3-ethyl-4-methylpyridine, 3,4-diethylpyridine, 3,5-diethylpyridine, 2-methyl-5-butylpyridine, 4-pentylpyridine, 4-(5-nonyl)pyridine, 2,6-dipropylpyridine, 2-methyl-3-ethyl-6-propylpyridine, 2,6-diethylpyridine, 2,6-dipropylpyridine, 2,6-dibutylpyridine, 2,6-di-tert.-butylpyridine; functional group-containing pyridines; such as 2-cyanopyridine, 3-cyanopyridine, 4-cyanopyridine, 2,6-dicyanopyridine, 3,5-dicyanopyridine,, 2-cyano-6- methylpyridine, 3-cyano-5-methylpyridine, picolinic amide, nicotinic amide, isonicotinic amide, picolinic acid, nicotinic acid, isonicotinic acid, dipicolinic acid, dinicotinic acid, cinchomethorinic acid, 5-butyl-picolinic acid, alkyl esters of nicotinic acid, 2-aminopyridine, 3-aminopyridine, 4-aminopyridine, 2,3-diaminopyridine, 2,5-diaminopyridine, 2,6-diaminopyridine, 2,3,6-triaminopyridine, 2-amino-3-methylpyridine, 2-amino-4-methylpyridine, 2-amino-5-methylpyridine, 2-amino-6-methylpyridine, 2-amino-4-ethylpyridine, 2-amino-4-propylpyridine, 2-amino-4-(5-nonyl) pyridine, 2-amino-4,6-dimethylpyridine. 2,6-diamino-4-methylpyridine, 2,2'-dipyridylamine, 4-(N,N-dimethylamino) pyridine, 2-hydroxypyridine, 3-hydroxypyridine, 4-hydroxypyridine, 2,6-dihydroxypyridine, 3-hydroxy-6-methylpyridine, 2-chloropyridine, 2,6-dichloropyridine, 4-chloropyridine, 2-amino-5-chloropyridine, 2-amino-3,5-dichloropyridine, 2-methyl-3,5-dichloro-6-methylpyridine, 2-amino-5-chloro-3-methylpyridine, 2-amino-3,5-dichloro-4-methylpyridine, 2-amino-3,5-dichloro-4,6-dimethylpyridine, 4-amino-3,5-dichloropyridine, pyridine-N-oxide, α-picoline-N-oxide, β-picoline-N-oxide, γ-picoline-N-oxide, 2,6-lutidine-N-oxide, 3,5-lutidine-N-oxide, 4-phenylpropylpyridine-N-oxide, 1,3-di-(4-pyridyl)propane-di-N-oxide, 4-(5-nonyl)-pyridine-N-oxide, 2-chloropyridine-N-oxide, 4-cyanopyridine-N-oxide, 2-pyridinemethanol-N-oxide, 3-pyridinemethanol, 4-pyridinemethanol, 2,6-pyridinemethanol, 2-pyridineethanol, 4-pyridineethanol, 3-picolyamine, 4-picolyamine, 2-methylaminoethylpyridine, 4-alkylaminoethyl-pyridines, 4-piperidinoethylpyridine, 4-(4-pipecolinoethyl)-pyridine, and 4-morpholinoethylpyridine, pyridines containing heterocyclic or homocyclic group, such as 2-phenylpyridine, 4-phenylpyridine, 2-benzylpyridine, 4-benzylpyridine, 4-phenylpropylpyridine, 4,4'-dipyridyl, 4,4'-dimethyl-2,2'-dipyridyl, 1,3-di-(4-pyridyl) propane, 1,2-di-(4-pyridyl)-ethane, 1,2-di-(4-pyridyl)-ethylene, 1,2,3-tri-(4-pyridyl) propane, 2,4,6-tri-(4-pyridyl)-S-triazine, 2,4-di(4-pyridyl)-6-methyl-S-triazine, and 2,5-di-(4-pyridyl)-S-tetrazine, alkenylpyridines or polymer pyridines, such as 2-vinylpyridine, 4-vinylpyridine, 2-vinyl-6-methylpyridine, 2-vinyl-5-ethylpyridine, 4-butenyl pyridine, pyridine, 4-vinylpyridine homopolymer, 2-vinylpyridine homopolymer, 2-vinylpyridine-acrylonitrile copolymer, 4-vinylpyridineacrylonitrile copolymer, 4-vinylpyridine-styrene copolymer, 4-vinylpyridine-divinylbenzene copolymer, 2-vinylpyridinedivinylbenzene copolymer, and 4-vinylpyridine homopolymer-N-oxide; pyrroles; pyrrolines; pyrinidines; pyrazines; pyrazoles; pyrazolines; pyridazines; imidazoles; 1,10-phenanthrolines, such as 1,10-phenanthroline 4-chloro-1, 10-phenanthroline, and 5-(thiabentyl)-1,10-phenanthroline; quinolines, such as quinoline, 2-(dimethylamino)-6-methoxyquinoline, 8-hydroxyquinoline and 2-carboxyquinoline.

(III) Compounds of pentavalent nitrogen group elements

The compounds include, for example ammonium acetate, ammonium propionate, and triphenylphosphineiminiumchloride and onium salts of said compounds (I) and (II).

Of these nitrogen group compounds, organic nitrogen group compounds containing nitrogen atom or phosphorus atom are preferable; organic compounds containing trivalent phosphorus atom or trivalent nitrogen atom are more preferable; and phosphine compounds containing trivalent phosphorus atom and heterocyclic compounds containing trivalent nitrogen atom, such as pyridines, or onium salts of the compounds are most preferable.

Though the reaction of methyl acetate or dimethyl ether with carbon monoxide proceeds in the presence of only the catalyst employed in this invention which comprises (a) the nickel component, (b) the halide and (c) the organic nitrogen group compound, the catalyst has only poor activity in the reaction. When the reaction is carried out in the presence of the catalyst together with a co-catalyst comprising one or more materials selected from metals belonging to Groups IA, IIIB and IVB of the Periodic Table, compounds of the metals and mixtures thereof and optionally one or more materials selected from metals belonging to IIA of the Periodic Table, compounds of the metals and mixtures thereof, the reaction proceeds speedily.

Metals or metal compounds which can be used as co-catalysts include metals having atomic weight of at least 5 and belonging to Groups IA, IIA, IIIB and IVB of the Periodic Table and compounds of these metals. Preferable metals or metal compounds include, for example, metals having atomic weight of less than 210, preferably less than 140 and belonging to said Groups and compounds of the metals.

Preferable metals of Group IA and compounds of the metals include lithium, sodium, potassium, rubidium and cesium, and compounds of the metals. Lithium, rubidium and cesium, and compounds of these metals are more preferable; and lithium and its compounds are most preferable.

Preferable metals of Group IIA and compounds of the metals include beryllium, magnesium, calcium, strontium and barium and compounds of the metals. Magnesium, calcium, strontium and barium and compounds of the metals are more preferable; and calcium and strontium and compounds of these metals are most preferable.

Preferable metals of Group IIIB and compounds of the metals include aluminum, gallium and thallium and compounds of the metals. Aluminum and aluminum compounds are most preferable.

Preferable metals of Group IVB and compounds of the metals include silicon, germanium and tin, and compounds of the metals. Tin and tin compounds are most preferable.

Preferable embodiments of metals and metals' combinations as a co-catalyst are as follows:
 (i) metal of group IVB or a compound of the metal;
 (ii) metal of Group IVB or a compound of the metal and metal of Group IIA or a compound of the metal;
 (iii) metal of Group IVB or a compound of the metal and metal of Group IA or a compound of the metal;
 (iv) metal of Group IVB or a compound of the metal, metal of Group IA or a compound of the metal and metal of Group IIA or a compound of the metal.

The metals belonging to Groups IA, IIA, IIIB and IVB of the Periodic Table may be used in form of element or in form of compounds. For example, they can be used as metal itself or Raney metals, or finely divided particles of the metals, or as metal compounds, such as carbonates, oxides, hydroxides, nitrates, sulfates, phosphates, halides, cyanides, thiocyanides, sulfonates, $C_1$–$C_5$ lower alkoxides, such as methoxides and ethoxides, phenoxide, metal carboxylates derived from $C_1$–$C_{20}$ alkanoic acids, oxyhalides, hydrides, nitrites, sulfites, phosphites, acetylacetonates and sulfides of metals, or metal compounds coordinated with ammonia, cyanide, amines or amino acids, or organic metal compounds having phenyl group or alkyl group.

Metals of Groups IA, IIA, IIIB and IVB and compounds of the metals include, for example $H_2SiO_3$, $H_4SiO_4$, $SiHBr_3$, $SiHCl_3$, $SiHF_3$, $SiHI_3$, Si $Si_2Br_6$, $SiBr_4$, $SiBrH_3$, $SiBrCl_3$, $SiBr_2Cl_2$, $SiBr_3Cl$, $Si_2Cl_6$, $SiCl_4$, $SiClH_3$, $SiF_4$, $SiH_4$, $Si_2H_6$, $Si_3H_8$, $Si_4H_{10}$, $SiI_2$, $Si_2I_6$, $SiI_4$, $SiICl_3$, $SiO_2$, $Si_2OCl_6$, $SiS$, $SiS_2$, Ge, $GeBr_4$, $GeCl_2$, $GeCl_4$, $GeHCl_3$, $GeF_4$. $3H_2O$, $GeH_4$, $GeI_4$, GeO, $GeO_2$, $GeOCl_2$, GeS, $GeS_2$, Sn, $SnBr_4$, $SnCl_4$, $SnF_4$, $SnI_4$, $SnO_2$, $SnOCl_2$, $2SnO_2.P_2O_5$. $10H_2O$, SnP, $Sn(SO_4)_2.2H_2O$, $SnS_2$, $SnBr_2$, $SnCl_2$, $SnF_2$, $Sn(OH)_2$, $SnI_2$, $SnC_2O_4$, SnO, $SnO.SnCl_2.3H_2O$, $SnSO_4$, SnS, $Sn(C_6H_5)_4$, $Sn(CH_3)_4$, $Sn(CH_3)_2$, $Sn(C_2H_5)_4$, $(C_3H_7)_2SnH_2$, $(CH_3)_2SnI_2$, $Sn(C_2H_5)_2$, $(C_4H_9)_2SnCl_2$, $(C_2H_5)_2SnI_2$, $(CH_3)_3SnCl$, $(C_4H_9)_2SnH_2$, $(C_3H_7)_2SnI_2,(CH_3)_3(CH_2I)$ Sn, $(C_4H_9)_3SnCl$, $(C_4H_9)_2SnI_2$, $(C_2H_5)_3SnCl$, $(C_4H_9)_3SnH$, $(C_2H_5)_3SnH$, $(C_6H_5CH_2)_3SNCl$, $Sn(C_2H_3O_2)_2$, $Sn(C_2H_3O_2)_4$, $PtH(SnCl_3)(CO)(Pph_3)_2$, Li, $LiC_2H_3O_2.2H_2O$, $LiAlO_2$, $LiNH_2$, $LiBO_2$, $Li_2B_4O_7.5H_2O$, LiBr, $LiBr.2H_2O$, $Li_2CO_3$, $LiHCO_3$, $LiClO_3$, $LiClO_3.0.5H_2O$, LiCl, $Li_3C_6H_5O_7.4H_2O$, $Li_2S_2O_6.2H_2O$, LiF, $Li_2[SiF_6].2H_2O$, $LiHCO_2.H_2O$, LiH, LiOH, $LiOH.H_2O$, LiI, $LiI.3H_2O$, $LiNO_3$, $LiNO_3.3H_2O$, $LiNO_2$. $H_2O$, $Li_2C_2O_4$, $LiHC_2O_4.H_2O$, $Li_2O$, $LiClO_4,LiClO_4.3H_2O$, $LiMnO_4$, $LiH_2PO_4$, $Li_3PO_4$, $Li_3PO_4.12H_2O$, $Li_2SiO_3$, $Li_4SiO_4$, $Li_2SO_4$, $Li_2SO_4.H_2O$, $LiHSO_4$, $Li_2S$, $Li_2SO_3$, Na, $NaC_2H_3O_2$(acetate), $NaAlO_2$, $NaNH_2$, $Na_2H_2Sb_2O_7.H_2O$, $Na_3AsO_4.12H_2O$, $NaBO_2$, NaBr, $Na_2CO_3$, $NaHCO_3$, NaCl, $2Na_3C_6H_5O_7.11H_2O$(citrate), NaCN, NaF, NaH, NaOH, NaOCl, NaI, $NaNO_3$, $NaNO_2$, $Na_3N$, $Na_2C_2O_4$.(oxalate), $Na_3PO_4$, $NaH_2PO_4.H_2O$, $NaKCO_3.6H_2O$, $Na_2SiO_3$, $Na_2SO_4$, $Na_2SO_3$, $Na_2S_2O_3$, K, $KC_2H_3O_2$.(acetate), $K_2(AlO_2)_2.3H_2O$, $KNH_2$, $KSbO_3$, $K_3AsO_4$, $KN_3$, $K_2B_2O_4$, KBr, $K_2CO_3$, $KHCO_3,KCl$, $K_2[SnBr_6]$,KCN, $K_3[Mn(CH)_6]$, KF, KH, KOH, $K_2O$, $K_3PO_4$, $KPO_3$, $KH_2PO_4$, $K_2SiO_3$, $K_2SO_4$, $K_2S_2O_5$, $K_3AsS_4$, KI, $KNO_3$, $KNO_2$, $K_2C_2O_4.H_2O$(oxalate), KClO, Rb, $RbBrO_3$, RbBr, $RbBr_3$, $Rb_2CO_3$, $RbHCO_3$, $RbClO_3$, RbCl, RbF, RbH, RbOH, $RbIO_3$, RbI, $RbI_3$, $RbNO_3$, $Rb_2O$, $Rb_2O_2$, $Rb_2O_3$, $Rb_2O_4$, $RbClO_4$, $RbIO_4$, $RbMnO_4$, $Rb_2SeO_4$, $Rb_2SO_4$, $Rb_2S$, $Rb_2S.4H_2O$, $Rb_2Ss$, $Rb(C_2H_3O_2)$, Cs, $CsBrO_3$, CSBR, $CsBr_3$, $Cs_2CO_3$, $CsHCO_3$, CsCl, CsCN, CsF, CsH, CsOH, $CsIO_3$, CsI, $CsI_3$, $CsNO_3$, $CsNO_2$, $Cs_2O$, $Cs_2O_2$, $Cs_2O_3$, $Cs_2O_4$, $CsClO_4$, $CsIO_4$, $CsMnO_4$, $Cs_8SiW_{12}O_{42}$, $Cs_2So_4$, $CsHSO_4$, $Cs_2S$ $4H_2O$, $Cs_2S_2$, $Cs_2S_2$. $H_2O$, $Cs_2S_3$, $Cs_2Ss$, $CsHC_4H_4O_6$, $Cs(C_2H_3O_2)$, Mg, $Mg(C_2H_3O_2)_2$, $Mg(C_2H_3O_2)_2.4H_2O$, $MgO.Al_2O_3$, $MgCl_2.NH_4Cl.6H_2o$, $MgNH_4PO_4$. $6H_2O$, $MgSO_4.(NH_4)_2SO_4.6H_2O$, $Mg(BO_2)_2.8H_2O$, $Mg(BrO_3)_2$. $6H_2O$, $MgBr_2$, $MgBr_2.6H_2O$, $MgCO_3$, $MgCO_3.3H_2O$, $3MgCO_3$. $Mg(OH)_2.3H_2O$, $Mg(ClO_3)_2.6H_2O$, $MgCl_2$, $MgCl_2.6H_2O$, $MgF_2$, $Mg[SiF_6].6H_2O$, $Mg(OH)_2$, $Mg(H_2PO_2)_2.6H_2O$, $Mg(IO_3)_2.4H_2O$, $MgI_2$, $Mg(NO_3)_2.6H_2O$, $Mg_3N_2$, $MgC_2O_4.2H_2O$, MgO, $Mg(ClO_4)_2$. $6H_2O$, $Mg(MnO_4)_2.6H_2O$, $Mg_3(PO_4)_2.4H_2O$, $Mg_3(PO_4)_2.8H_2O$, $MgHPO_4.3H_2O$, $MgHPO_4.7H_2O$, $Mg_2P_2O_7$, $Mg_2P_2O_7.3H_2O$, $MgHPO_3$. $3H_2O$, $MgCl_2.KCl.6H_2O$, $MgSO_4.K_2SO_4.6H_2O$, $MgCl_2.NaCl.H_2O$, $MgSO_4$, $MgSO_4.7H_2O$, MgS, $MgSO_3.6H_2O$, $Mg(C_4H_4O_6).5H_2O$, $MgS_2O_3.6H_2O$, Ca, $Ca(C_2H_3O_2)_2.H_2O$, $Ca(AlO_2)_2$, $CaO.Al_2O_3$. $2SiO_2$, $CaNH_4AsO_4.6H_2O$, $CaNH_4PO_4.7H_2O$, $Ca_3(AsO_4)_2$, $Ca(BO_2)_2.2H_2O$, $CaB_6$, $Ca(BrO_3)_2.H_2O$, $CaBr_2$, $CaBr_2.6H_2O$, $CaC_2$, $CaCO_3$, $Ca(ClO_3)_2.2H_2O$, $CaCl_2$, $CaCl_2.H_2O$, $CaCl_2$. $6H_2O$, $Ca_3(C_6H_5O_7)_2.4H_2O$, $Ca(CN)_2$, $CaCN_2$, $CaS_2O_6.4H_2O$, $CaF_2$, $Ca[SiF_6]$, $Ca[SiF_6].2H_2O$, $Ca(HCO_2)_2$, $CaH_2$, $Ca(SH)_2$. $6H_2O$, $Ca(OH)_2$, $Ca(ClO)_2.4H_2O$, $Ca(IO_3)_2$, $CaI_2$, $CaI_2$. $6H_2O$, $Ca(C_3H_5O_3)_2.5H_2O$, $CaO.MgO.2CO_2$, $CaO.MgO.2SiO_2$, $CaMoO_4$, $Ca(NO_3)_2$, $Ca(NO_3)_2.4H_2O$, $Ca_3N_2$, $Ca(NO_2)_2.H_2O$, $CaC_2O_4$, CaO, $Ca(MnO_4)_2.4H_2O$, $CaO_2.8H_2O$, $CaHPO_4.2H_2O$, $Ca_2P_2O_6.2H_2O$, $Ca(PO_3)_2$, $Ca(H_2PO_4)_2.H_2O$, $Ca_2P_2O_7$, $Ca_2P_2O_7$. $5H_2O$, $Ca_3(PO_4)_2$. $2H_2O$, $2CaHPO_3.3H_2O$, $Ca(H_2PO_2)_2$, $CaK_2(SO_4)H_2$. $H_2O$, $CaSiO_3$, $CaSi_2$, $CaSO_4.2Na_2SO_4.2H_2O$, $CaSO_4$, $CaSO_4$. $2H_2O$, $CaSO_4.0.5H_2O$, CaS, $CaSO_3.2H_2O$, $CaC_4H_4O_6.4H_2O$, $CaCS_3$, $Ca(SCN)_2.3H_2O$, $CaS_2O_3.6H_2O$, $CaWO_4$, Sr, $Sr(C_2H_3O_2)_2$, $SrB_4O_7.4H_2O$, $Sr(BrO_3)_2.H_2O$, $SrBr_2$, $SrBr_2.6H_2O$, $SrCO_3$, $Sr(ClO_3)_2$, $Sr(ClO_3)_2.8H_2O$, $SrCl_2$, $Sr(CN)_2.4H_2O$, $SrS_2O_6$. $4H_2O$, $SrF_2$, $Sr[SiF_6].2H_2O$, $Sr(HCO_2)_2$, $Sr(HCO_2).2H_2O$, $Sr(SH)_2$, $Sr(OH)_2$, $Sr(OH)_2.8H_2O$, $Sr(IO_3)_2$, $SrI_2$, $SrI_2$. $6H_2O$, $Sr(NO_3)_2$, $Sr(NO_3)_2.4H_2O$, $Sr(NO_2)_2$, $Sr(NO_2)_2.H_2O$, $SrC_2O_4.H_2O$, SrO, $SrO_2$, $SrO_2.8H_2O$, $Sr(MnO_4)_2.3H_2O$, $SrHPO_4$, $SrSiO_3$, $SrSO_4$, $Sr(HSO_4)_2$, SrS, $SrS_4.6H_2O$, $SrSO_3$, $Sr(CNS)_2.3H_2O$, $SrS_2O_3.5H_2O$, Ba, $Ba(C_2H_3O_2)_2$, $Ba(C_2H_3O_2)_2.H_2O$, $Ba(NH_3)_2$, $Ba_3(AsO_4)_2$, $BaHAsO_4.H_2O$, $Ba(N_3)_2$, $Ba(N_3)_2.H_2O$, $Ba(BrO_3)_2.H_2O$, $BaBr_2$, $BaBr_2.2H_2O$, $Ba[PtBr_6].10H_2O$, $BaC_2$, $BaCO_3$, $Ba(ClO_3)_2$, $Ba(ClO_3)_2.H_2O$, $BaClO_2$, $BaCl_2.2H_2O$, $Ba(CH)_2$, $BaS_2O_6.2H_2O$, $BaF_2$ $Ba[SiF_6]$, $Ba(HCO_2)_2$, $BaH_2$, $Ba(SH)_2.4H_2O,Ba(OH)_2$, $Ba(OH)_2.8H_2O$, $Ba(ClO)_2$, $BaPO_3$, $Ba(H_2PO_2)_2.H_2O$, $Ba(IO_3)_2$, $Ba(IO_3)_2$. $H_2O$, $BaI_22H_2O$, $BaI_2.6H_2O$, $BaMnO_4$, $BaMoO_4$, $Ba(NO_3)_2$, $Ba(NO_2)_2$, $Ba(NO_2)_2.H_2O$, $BaC_2O_4$, BaO, $Ba(ClO_4)_2$, $Ba(ClO_4)_2$. $3H_2O$, $Ba(MnO_4)_2$, $BaO_2$, $BaO_28H_2O$, $BaS_2O_8.4H_2O$, $BaHPO_4$, $Ba(H_2PO_4)_2$, $Ba_2P_2O_7$, $Ba_3(PO_4)_2$, $BaSiO_3BaSiO_3.6H_2O$, $BaSO_4$, BaS, $BaS_4$ $2H_2O$, $BaS_3$, $BaSO_3$, $Ba(CNS)_2.2H_2O$, $BaS_2O_3.H_2O$, Al, $Al(C_2H_3O_2)_3$, $Al(BrO_3)_3.9H_2O$, $AlBr_3$, $Al_4C_3$, $Al(ClO_3)_3.6H_2O$, $AlCl_3$, $AlF_3,Al_2F_6.7H_2O$, $Al(OH)_3$, $AlI_3$, $Al(NO_3)_3.9H_2O$, $Al_2N_2$, $Al_3O_3$, $AlPO_4$, $AlCl_3.NaCl$, $AlF_3.3NaF$ and $Al_2(SO_4)_3$.

Since a halide, such as a bromide or an iodide is used as one component of the catalyst and the object product is an organic acid anhydride, it is preferable that the co-catalyst metal be used in form of a halide, such as bromide or iodide, or organic acid salt, such as acetate.

The amount of the nickel component employed as one component of the catalyst in this invention may be in the range of $1\times10^{-6}$mol$-5$ mol, preferably $1\times10^{-4}$mol$-4$ mol, more preferably $1\times10^{-3}$mol$-2$ mol and most preferably $5\times10^{-3}$mol$-1.0$ mol per 1 liter of a reaction solution in terms of metal.

The amount of the halide employed as one component of the catalyst may be in the range of from $10^{-3}$mol$-15$ mol, preferably $10^{-2}$mol$-10$ mol and preferably $10^{-}$mol$-8$ mol per 1 liter of a reaction solution in terms of halogen atom.

The amount of the organic nitrogen group compound employed as one component of the catalyst depends upon the kind and amount of the nickel component. However, in general, the amount of the compounds employed may be in the range of $1\times10^{-6}$mol$-10$ mol, preferably $1\times10^{-4}$mol$-5$ mol and most preferably $1\times10^{-3}$mol$-2.5$ mol per 1 liter of a reaction solution.

The amount of each of metals of Group IA or compounds of the metal, metals of Group IIA or compounds of the metal, metals of Group IIIB or compounds of the metal and metals of Group IVB or compounds of the metal employed as the co-catalyst of this invention may be in the range of 0.01 mol–100 mol, preferably 0.03 mol–80 mol and most preferably 0.1 mol–50 mol per 1 mol of nickel in terms of metal. However, in general, the amount of each of the metals or the metal compounds employed as the co-catalyst may be in the range of $1 \times 10^{-6}$ mol–50 mol, preferably $1 \times 10^{-4}$ mol–30 mol and most preferably $1 \times 10^{-3}$ mol–20 mol per 1 liter of a reaction solution in terms of metal. In general, the amount of the metal of Group IA or IIA or compound of the metal employed may be in the range of $1 \times 10^{-3}$ mol–$1 \times 10^3$ mol, preferably $1 \times 10^{-2}$ mol–$5 \times 10^2$ mol and most preferably 0.1 mol–100 mol per mol of the metal of Group IVB or compound of the metal in terms of metal.

In practicing this invention, the reaction temperature is not critical. In general, the reaction temperature may be within the range of 20° C.–350° C., preferably 80° C.–300° C. and most preferably 100° C.–250° C.

The reaction pressure is kept high enough to keep the raw material(s), the solvent and the product in a liquid phase and to maintain appropriately partial pressure of carbon monoxide. The partial pressure of carbon monoxide may be in the range of 0.5 Kg/cm²–300 Kg/cm² preferably 1 Kg/cm²–200 kg/cm², and most preferably 3 Kg/cm²–150 Kg/cm². However, partial pressure of the carbon monoxide may be in the range of 0.05 Kg/cm²–5000 Kg/cm².

Dimethyl ether and methyl acetate which are used as starting materials in this invetnion may be prepared by known methods. For example, dimethyl ether may be produced from CO and H₂ directly or by dehydration-dimerization reaction of methanol.

Methyl acetate may be produced by esterification of methanol and acetic acid. In this reaction acetic acid may be produced by reacting methanol with carbon monoxide (refer to Patent Publication (Kokai) Nos. 59211/1979, 63002/1979 and 66614/1979). Acetic acid formed as a by-product in product of cellulose acetate can be utilized in the esterification reaction. Methyl acetate formed together with PVA in process for converting vinyl acetate to PVA may be used as a starting material in the present invention. Methyl acetate produced by reaction methanol with synthesis gas as exemplified in Japanese Patent Publication (Kokoku) No. 2525/1973, and Japanese Patent Publication (Kokai) No. 149213/1976, 136110/1977 and 136111/1977 may be used in the present invention. Methyl acetate produced in the above methods may contain methanol, dimethyl ether, acetic acid, acetaldehyde, dimethyl acetal and halides, such as methyl iodide as impurities. However, incorporation of these compounds in methyl acetate is permitted as long as an overall balance is obtained.

Dimethyl ether is considered to be a precursor of methyl acetate in the carbonylation reaction. Therefore, when the term "methyl acetate" is used as a starting material for preparing acetic anhydride, dimethyl ether should be included in the methyl acetate.

The carbon monoxide employed as a raw material gas does not need to be highly pure and may contain hydrogen, carbon dioxide, methane, nitrogen, rare gases and water. Hydrogen does not interfere with the carbonylation reaction but, rather, stabilizes the catalyst.

When metals of Group VIII of the Periodic Table excluding nickel, such as rhodium or palladium or compounds of the metals are used as catalyst, by-products, such as ethylidene diacetate and acetaldehyde are formed in the presence of carbon monoxide and hydrogen, as exemplified in Japanese Patent Publication (Kokai) No. 115409/1976. However, even if carbon monoxide and hydrogen are present in the reaction system, such by-products are not formed in the presence of a nickel component as a metal component constituting a catalyst. Therefore, the nickel component exhibits different properties from those of a rhodium or palladium system. An extremely low concentration of carbon monoxide in the reaction system is not desirable, because the reaction pressure must rise when using the gas.

In general, water is incorporated into the reaction system, because commercially available raw material gas and methyl acetate or dimethyl ether contain a small amount of water. Raw material gas and methyl acetate of dimethyl ether containing water of such low concentration are permitted in this invention. The presence of water or more than 10 mol % on the basis of weight of a reaction solution is not preferable in this process, because such a large amount of water causes the starting materials and the products to decompose.

In general, a water content of less than 5 mol % is preferable, and a water content less than 3 mol % is more preferable. When the raw materials contains a large amount of water, they should be dried before introducing them into the reaction system.

Since methyl acetate or dimethyl ether (as a starting material) and/or acetic anhydride (object product) serves as a solvent for the reaction of this invetion, another solvent may not be used. Any organic solvent or diluent compatible with the starting material and the object product under the reaction conditions may be used.

Solvents which participate in the reaction as a component constituting catalyst, a raw material, an intermediate, or a product are preferable. Such solvents are methyl iodide, methyl acetate, acetic anhydride and acetic acid.

Solvents or diluents other than those which participate in the reaction can be used in this invention. Examples of such solvents include organic acid esters such as ethylene glycol diacetate, propylene glycol diacetate, dimethyl adipate, methyl benzoate, and dimethyl phthalate; hydrocarbons, such as dodecane, hexadecane, benzene, naphthalene, and biphenyl; and inorganic acid esters, such as triphenyl phosphate, tricresyl phosphate, dibutylphenyl phosphate, tetramethyl orthosilicate and tetrabutyl silicate.

The present process may be carried out by batch, semi-continuous or continuous method. When the invention is carried out as a continuous process, acetic anhydride, unreacted methyl acetate or dimethyl ether, the halides, the organic nitrogen group compound and the metal catalytic components may be recovered by a separating operation, such as distillation from reaction mixture withdrawn from carbonylation reaction. The halides, the organic nitrogen group compound and the metal catalytic components which have been recovered may be recirculated into the reaction system.

The separating zone comprises one or more distilling units, for example, the flash distillation and/or purifying columns. Acetic anhydride can be withdrawn in a gaseous state by distillation in the carbonylation reaction zone from the reaction mixture. The gaseous mixture contains non-condensable gas, such as carbon monoxide and hydrogen (it is contained only in a certain case) and acetic anhydride, unreacted methyl acetate or dimethyl ether, halides and nickel compounds (it is contained only in a certain case). In general, the co-catalyst is non-volatile, so it remains in the reaction zone together with the nickel component. The gaseous mixture may be cooled and condensed. The non-condensable components may be recycled into the carbonylation reaction zone and fresh carbon monoxide and hydrogen (if necessary) may be introduced into the reaction zone to increase the pressure of carbonylation reaction zone to a desired extent.

Components condensed from the reaction mixture may be subjected to distillation to separate each component. The resulting unreacted methyl acetate or dimethyl ether and halides may be recycled into the reaction zone.

Part of the reaction mixture gas may be purged from the reaction system to prevent accumulation of impurities, such as nitrogen introduced into the system with carbon monoxide and hydrogen and by-products, such as methane formed in the reaction system.

The present invention is characterized by production of acetic anhydride by reaction of methyl acetate or dimethyl ether and carbon monoxide by using highly active non-expensive catalyst and co-catalyst, so the present invention is preferable from an industrial point of view.

The following examples are given as illustrative embodiment of the invention and should not be construed as limiting its scope.

All parts and percents are on weight, unless otherwise specified. In examples, Ac represents acetyl group.

EXAMPLE 1

Into an autoclave were charged 0.208 gram of nickel powder, 0.76 g of 2,4-lutidine, 1.32 g of lithium acetate and 13.9 g of methyl iodide and 24.0 g of acetic acid and 29.6 g of methyl acetate. Carbon monoxide was fed under pressure to pressure of 80 Kg/cm$^2$ (partial pressure of H$_2$ is 10 Kg/cm$^2$ and partial pressure of CO is 50 Kg/cm$^2$). The temperature was raised to 200° C. The reaction of methyl acetate and carbon monoxide was carried out at 200° C. for 2 hours while maintaining the pressure at 80 Kg/cm$^2$ by continuously feeding carbon monoxide into the autoclave. After cooling the reaction mixture, analysis showned that yield of acetic anhydride was 58% methyl acetate.

EXAMPLES 2–9

The reactions of methyl acetate or dimethyl ether and carbon monoxide were carried out in the same way as in Example 1.

The feeding materials, reaction conditions and results are shown in Table 1.

In Example 9, catalytic components and solvent were charged in the autoclave. After air in the autoclave was replaced with carbon monoxide, dimethyl ether was fed into the autoclave. Thereafter, carbon monoxide was fed under pressure to pressure as given in Table 1.

TABLE 1

| | starting material (g) | solvent (g) | nickel component (g) | organic nitrogen group compound (g) | halide (g) | co-catalyst I (g) | co-catalyst II (g) | temperature (°C.) | total pressure (kg/cm$^2$) | partial pressure of CO(H$_2$) (kg/cm$^2$) | time (hr) | yield of acetic anhydride (%) |
|---|---|---|---|---|---|---|---|---|---|---|---|---|
| 1 | AcOCH$_3$ 29.6 | AcOH 24.0 | Ni powder 0.208 | 2,4-lutidine 0.76 | CH$_3$I 13.9 | LiOAc 1.32 | | 200 | 80 | 50(10) | 2.0 | 58 |
| 2 | AcOCH$_3$ 29.6 | AcOH 24.0 | Ni powder 0.415 | 2,4-lutidine 1.52 | CH$_3$I 13.9 | AlI$_3$ 2.88 | | 200 | 100 | 60(20) | 2.0 | 64 |
| 3 | AcOCH$_3$ 29.6 | AcOH 24.0 | Ni powder 0.415 | 2,4-lutidine 1.52 | CH$_3$I 13.9 | SnI$_4$ 4.43 | | 200 | 100 | 60(20) | 2.0 | 65 |
| 4 | AcOCH$_3$ 29.6 | AcOH 24.0 | Ni powder 0.415 | triphenyl phosphine 3.70 | CH$_3$I 13.9 | LiOAc 2.64 | | 200 | 80 | 50(10) | 2.0 | 65 |
| 5 | AcOCH$_3$ 29.6 | AcOH 24.0 | NiI$_2$ 2.21 | 2,4-lutidine 1.52 | CH$_3$I 13.9 | LiOAc 5.28 | | 180 | 80 | 55(10) | 2.0 | 59 |
| 6 | AcOCH$_3$ 29.6 | AcOH 24.0 | Ni powder 0.417 | tri-n-butyl amine 2.63 | CH$_3$I 13.9 | LiI 5.36 | | 200 | 80 | 50(10) | 2.0 | 63 |
| 7 | AcOCH$_3$ 29.6 | AcOH 24.0 | Ni powder 0.417 | 2,4-lutidine 1.52 | CH$_3$I 13.9 | Ba(OAc)$_2$ 1.80 | SnI$_4$ 4.43 | 180 | 80 | 55(10) | 2.0 | 70 |
| 8 | AcOCH$_3$ 55.5 | | NiI$_2$ 2.21 | 2,6-lutidine 1.52 | CH$_3$I 23.0 | LiOAc 2.64 | | 180 | 80 | 55(10) | 5.0 | 51 |
| 9 | CH$_3$OCH$_3$ 18.4 | AcOH 24.0 | NiI$_2$ 2.21 | 2,4-lutidine 1.52 | CH$_3$I 13.9 | LiOAc 2.64 | | 180 | 80 | 55(10) | 4.0 | 52 |

EXAMPLES 10–16

The reactions of methyl acetate and carbon monoxide were carried out in the same way as in Example 1. The feeding materials, reaction conditions and results are shown in Table 2. It took 12 minutes and 11.5 minutes to convert 25% of methyl acetate to acetic anhydride in Example 10 and 13, respectively. The reaction rates are caluculated to 7.1 and 7.5 mol/l.hr, respectively, by considering volume of the autoclave.

Any products derived from reduction of acetic anhydride, such as ethylidene diacetate was not formed in all examples.

TABLE 2

| No. | starting material (g) | solvent (g) | nickel component (g) | organic nitrogen group compound (g) | halide (g) | co-catalyst I (g) | co-catalyst II (g) | temperature (°C.) | total pressure (kg/cm$^2$) | partial pressure of CO(H$_2$) (kg/cm$^2$) | time (hr) | yield of acetic anhydride (%) |
|---|---|---|---|---|---|---|---|---|---|---|---|---|
| 10 | AcOCH$_3$ 29.6 | AcOH 24.0 | Ni powder 0.415 | 2,4-lutidine 1.52 | CH$_3$I 13.9 | SnI$_4$ 4.43 | LiOAc 2.56 | 180 | 80 | 55(10) | 1.0 | 80 |
| 11 | AcOCH$_3$ 29.6 | AcOH 24.0 | Ni powder 0.415 | 2,4-lutidine 1.52 | CH$_3$I 13.9 | AlI$_3$ 2.88 | LiOAc 2.56 | 180 | 80 | 55(10) | 2.0 | 62 |
| 12 | AcOCH$_3$ 29.6 | AcOH 24.0 | Ni powder 0.415 | 2,4-lutidine 1.52 | CH$_3$I 13.9 | SnI$_4$ 4.43 | CaI$_2$ 2.08 | 180 | 80 | 55(10) | 1.5 | 60 |
| 13 | AcOCH$_3$ 29.6 | AcOH 24.0 | Ni powder 0.415 | 2,4-lutidine 1.52 | CH$_3$I 13.9 | SnI$_4$ 4.43 | SrI$_2$ 13.7 | 180 | 80 | 50(15) | 1.0 | 81 |
| 14 | AcOCH$_3$ 29.6 | Ac$_2$O 24.0 | Ni powder 0.415 | 2,4-lutidine 1.52 | CH$_3$I 13.9 | SnI$_4$ 4.43 | LiOAc 2.56 | 180 | 80 | 50(15) | 1.0 | 62 |
| 15 | AcOCH$_3$ 29.6 | AcOH 24.0 | Ni powder 0.415 | 2,4-lutidine 1.52 | CH$_3$I 13.9 | BaI$_2$ 2.76 | LiOAc 2.56 | 180 | 80 | 65(0) | 2.0 | 65 |
| 16 | AcOCH$_3$ 29.6 | AcOH 42.0 | NiI$_2$ 2.21 | α-picoline 1.32 | HI 6.3 | SnI$_4$ 4.43 | SrI$_2$ 13.7 | 180 | 80 | 55(10) | 2.0 | 55 |

EXAMPLES 17–29

The reactions of methyl acetate and carbon monoxide were carried out by using the materials as given in Table 3 under the reaction conditions as given in Table 3. The reaction were continued while feeding carbon monoxide into an autoclave.

TABLE 3

| Ex No. | starting material (g) | solvent (g) | nickel component (g) | organic nitrogen group compound (g) | halide (g) | co-catalyst (g) | co-catalyst (g) | co-catalyst (g) | temperature (°C.) | total pressure (kg/cm$^2$) | partial pressure of CO(H$_2$) (kg/cm$^2$) | time (hr) | yield of acetic anhydride (%) |
|---|---|---|---|---|---|---|---|---|---|---|---|---|---|
| 17 | AcOCH$_3$ 30 | AcOH 25 | Ni powder 0.5 | 2,4-lutidine 2 | CH$_3$I 14 | Sn(OAc)$_2$ 1.7 | LiOAc 2.6 | | 185 | 80 | 55(10) | 1.0 | 81 |
| 18 | AcOCH$_3$ 30 | AcOH 25 | Ni powder 0.5 | 2,4-lutidine 2 | CH$_3$I 14 | SnI$_4$ 4.4 | LiOAc 2.6 | | 180 | 70 | 45(10) | 1.0 | 89 |
| 19 | AcOCH$_3$ 30 | AcOH 12 | Ni powder 0.4 | 2,4-lutidine 1.5 | CH$_3$I 14 | SnI$_4$ 4.4 | SrI$_2$ 13.7 | | 175 | 80 | 48(15) | 1.0 | 91 |
| 20 | AcOCH$_3$ 30 | AcOH 25 | Ni powder 0.5 | 2,4-lutidine 2 | CH$_3$I 14 | SnI$_4$ 4.4 | CaI$_2$ 2 | | 185 | 75 | 60(5) | 1.5 | 67 |
| 21 | AcOCH$_3$ 30 | AcOH 25 | NiI$_2$ 2.2 | 2,4-lutidine 1.5 | CH$_3$I 14 | Si(OCH$_3$)$_4$ 1.1 | LiOAc 2.6 | | 190 | 80 | 50(10) | 2.0 | 65 |
| 22 | AcOCH$_3$ 30 | AcOH 25 | Ni powder 0.4 | triphenyl phosphine 3.7 | CH$_3$I 14 | SnI$_2$ 3.3 | LiI 5.3 | | 180 | 80 | 55(10) | 1.0 | 75 |
| 23 | AcOCH$_3$ 30 | AcOH 25 | Ni powder 0.5 | 2,4-lutidine 2 | CH$_3$I 14 | GeI$_4$ 4.1 | LiOAc 2.6 | | 185 | 80 | 55(10) | 2.0 | 61 |
| 24 | AcOCH$_3$ 30 | AcOH 25 | NiI$_2$ 2.2 | (n-Bu)$_3$N 2.6 | CH$_3$I 14 | SnI$_4$ 4.4 | LiOAc 1.3 | BaI$_2$ 3.9 | 170 | 80 | 67(0) | 1.0 | 77 |
| 25 | AcOCH$_3$ 30 | Ac$_2$O 25 | Ni powder 0.5 | 2,4,6-trimethyl pyridine 2 | CH$_3$I 14 | SnI$_4$ 4.4 | LiOAc 2.6 | | 185 | 80 | 55(10) | 1.0 | 72 |
| 26 | AcOCH$_3$ 30 | AcOH 41 | NiI$_2$ 2.2 | 3,5-lutidine 2 | HI 6 | SnI$_4$ 4 | LiI 5 | | 185 | 80 | 50(15) | 2.0 | 61 |
| 27 | AcOCH$_3$ 30 | AcOH 25 | Ni powder 0.4 | N,N—dimethyl acetamide 1.2 | CH$_3$I 14 | SnHPO$_4$ 1.5 | LiOAc 2.6 | | 185 | 70 | 50(5) | 0.5 | 61 |
| 28 | AcOCH$_3$ 30 | | NiI$_2$ 2.2 | 2,6-lutidine 2 | CH$_3$I 14 | SnI$_4$ 4.4 | LiOAc 2.6 | | 180 | 80 | 50(15) | 1.0 | 81 |
| 29 | AcOCH$_3$ 30 | AcOH 25 | Ni powder | 2,4-lutidine | CH$_3$I 7 | SnI$_4$ 4.4 | LiOAc 2.6 | | 180 | 80 | 65(0) | 1.0 | 73 |

TABLE 3-continued

| | | | organic | | | | | | | reaction conditions | | | yield |
| | | nickel | nitrogen | | | | | | | | partial pressure | | of acetic |
| Ex | starting | | com- | group | | | | | temper- | total | of | | an- |
| | material | solvent | ponent | compound | halide | | co-catalyst | | ature | pressure | $CO(H_2)$ | time | hydride |
| No. | (g) | (g) | (g) | (g) | (g) | (g) | (g) | (g) | (°C.) | (kg/cm$^2$) | (kg/cm$^2$) | (hr) | (%) |
|---|---|---|---|---|---|---|---|---|---|---|---|---|---|
| | | | 0.4 | 1.5 | | | | | | | | | |

EXAMPLE 30

Into an autoclave were charged 15 g of methyl acetate, 24 g of acetic acid, 0.5 g of nickel powder, 2.0 g of 2,4-lutidine, 14 g of methyl iodide, 3.3 g of $SnI_4$ and 1.3 g of LiOAc. Carbon monoxide was fed under pressure into the autoclave to pressure of 50 Kg/cm$^2$ (partial pressure of CO is about 30 Kg/cm$^2$ and partial pressure of $H_2$ is about 10 Kg/cm$^2$). The reaction of methyl acetate and carbon monoxide was carried out at 180° C. for 2 hours. After completing the reaction, analysis showned that yield of acetic anhydride was 94% on the basis of methyl acetate.

EXAMPLE 31

9.2 g of dimethyl ether was fed under pressure into the reaction mixture of Example 30. Carbon monoxide was fed under pressure into the autoclave to pressure of 80 Kg/cm$^2$ (partial pressure of CO is 45 Kg/cm$^2$ and partial pressure of $H_2$ is 10 Kg/cm$^2$). The reaction of dimethyl ether and carbon monoxide was carried out at 180° C. for 2 hours while feeding carbon monoxide into the autoclave. After completing the reaction, analysis showed that yield of acetic anhydride was 77% on the basis of dimethyl ether.

What is claimed is:

1. A process for producing acetic anhydride which comprises reacting methyl acetate or dimethyl ether with carbon monoxide at a temperature between 100° C. and 250° C. and at a partial carbon monoxide pressure between 3 kg/cm$^2$ and 150 kg/cm$^2$ in the presence of a catalyst comprising (a) nickel or a nickel compound, (b) at least one halide selected from the group consisting of bromides, iodides and mixtures thereof and (c) at least one hetero cyclic compound containing at least one trivalent nitrogen atom, together with a co-catalyst, said co-catalyst comprising one or more compounds selected from the group consisting of lithium iodide, lithium acetate, stannous iodide, stannous acetate, stannic iodide and aluminum iodide.

2. The process as defined in claim 1 wherein said co-catalyst is at least one compound selected from the group consisting of stannous iodide, stannous acetate and stannic iodide.

3. The process as defined in claim 1 wherein said co-catalyst is a mixture of (i) at least one compound selected from the group consisting of stannous iodide, stannous acetate and stannic iodide and (ii) at least one compound selected from the group consisting of lithium iodide and lithium acetate.

4. The process as defined in claim 1 wherein said co-catalyst further contains one or more compounds selected from the group consisting of magnesium iodide, calcium iodide, strontium iodide and barium iodide.

5. The process as defined in claim 2 wherein said co-catalyst further contains at least one compound selected from the group consisting of magnesium iodide, calcium iodide, strontium iodide and barium iodide.

6. The process as defined in claim 3 wherein said co-catalyst further contains at least one compound selected from the group consisting of magnesium iodide, calcium iodide, strontium iodide and barium iodide.

7. The process as defined in claim 1 wherein the amount of said nickel or nickel compound employed is in the range of from $1 \times 10^{-6}$ mol to 5 mol per 1 liter of a reaction solution in terms of metallic nickel.

8. The process as defined in claim 1 wherein the amount of each of said one or more compounds of said co-catalyst is in the range of 0.01 mol to 100 mol per 1 mol of nickel in terms of metal.

9. The process as defined in claim 4 wherein the amount of said one or more compounds selected from the group consisting of magnesium iodide, calcium iodide, strontium iodide, and barium iodide in the range of 0.01 mol to 100 mol per 1 mol of nickel in terms of metal.

10. The process as defined in claim 1 wherein the amount of each of said one or more compounds of said co-catalyst is in the range of 0.03 mol to 80 mol per 1 mol of nickel in terms of metal.

11. The process as defined in claim 1 wherein the amount of each of said one or more compounds of said co-catalyst is in the range of 0.1 mol to 50 mol per 1 mole of nickel in terms of metal.

12. The process as defined in claim 4 wherein the amount of said one or more compounds selected from the group consisting of magnesium iodide, calcium iodide, strontium iodide, and barium iodide is in the range of 0.03 mol to 80 mol per 1 mol of nickel in terms of metal.

13. The process as defined in claim 4 wherein the amount of said one or more compounds selected from the group consisting of magnesium iodide, calcium iodide, strontium iodide and barium iodide is in the range of 0.1 mol to 50 mol per 1 mol of nickel in terms of metal.

14. The process as defined in claim 1 wherein said co-catalyst is at least one compound selected from the group consisting of lithium iodide and lithium acetate.

15. The process as defined in claim 1 wherein said co-catalyst is aluminum iodide.

16. The process as defined in claim 1 wherein said co-catalyst further contains calcium iodide.

17. The process as defined in claim 1, wherein said hetero cyclic compound is selected from the group consisting of pyridine and pyridine derivatives.

18. The process as defined in claim 17, wherein said hetero cyclic compound is selected from the group consisting of 2,4-lutidine, 2,6-lutidine, 3,5-lutidine, alpha-picoline and 2,4,6-trimethylpyridine.

* * * * *